(12) United States Patent
Vik et al.

(10) Patent No.: US 9,616,247 B2
(45) Date of Patent: Apr. 11, 2017

(54) TREATMENT PLAN EVALUATION IN RADIOTHERAPY BY STOCHASTIC ANALYSIS OF DELINEATION UNCERTAINTY

(75) Inventors: Torbjoern Vik, Hamburg (DE); Julien Senegas, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2242 days.

(21) Appl. No.: 12/531,494

(22) PCT Filed: Mar. 6, 2008

(86) PCT No.: PCT/IB2008/050830
§ 371 (c)(1),
(2), (4) Date: Sep. 16, 2009

(87) PCT Pub. No.: WO2008/120116
PCT Pub. Date: Oct. 9, 2008

(65) Prior Publication Data
US 2010/0086183 A1    Apr. 8, 2010

Related U.S. Application Data

(60) Provisional application No. 60/909,013, filed on Mar. 30, 2007.

(51) Int. Cl.
*G06K 9/00*    (2006.01)
*A61N 5/10*    (2006.01)
*G06T 7/00*    (2017.01)
*G06T 7/10*    (2017.01)

(52) U.S. Cl.
CPC .......... *A61N 5/1031* (2013.01); *G06T 7/0012* (2013.01); *G06T 7/10* (2017.01); *A61N 5/1037* (2013.01); *A61N 5/1038* (2013.01); *G06T 2207/10072* (2013.01); *G06T 2207/20104* (2013.01); *G06T 2207/30096* (2013.01)

(58) Field of Classification Search
USPC ..................................... 382/228, 128; 705/3
See application file for complete search history.

(56) References Cited

U.S. PATENT DOCUMENTS

| | | |
|---|---|---|
| 5,602,892 A | 2/1997 | Llacer |
| 6,249,594 B1 | 6/2001 | Hibbard |
| 7,046,762 B2 | 5/2006 | Lee |
| 2003/0065260 A1* | 4/2003 | Cheng et al. ................ 600/427 |
| 2005/0197564 A1* | 9/2005 | Dempsey ..................... 600/411 |
| 2007/0242796 A1* | 10/2007 | Vengrinovich et al. ........ 378/11 |

* cited by examiner

*Primary Examiner* — Lena Najarian

(57) ABSTRACT

The present application is directed to the idea of using sampling techniques to propagate segmentation uncertainty in order to evaluate variability in radiation planning. A radiotherapy planning apparatus (10) creates diagnostic image data of a region of interest of a subject. Image data from other sources can also be used. The image data is segmented (44) and combined with previously imaged model data. Target measures such as dose volume histograms are produced for each of the segmentations of the image data. These measures are later combined into a statistical quantification of the target measure (FIG. 3). This information is presented (52) to the user to give the user possible outcomes of the radiotherapy plan, and, e.g., confidence levels in those outcomes.

11 Claims, 3 Drawing Sheets

TREATMENT PLAN EVALUATION IN RADIOTHERAPY BY STOCHASTIC ANALYSIS OF DELINEATION UNCERTAINTY

CROSS REFERENCE TO RELATED APPLICATIONS

This application claims the benefit of U.S. provisional application Ser. No. 60/909,013 filed Mar. 30, 2007, which is incorporated herein by reference.

The present application relates to the radiotherapy treatment arts. It finds particular application in planning radiation treatment regimens and will be described with particular reference thereto. It is to be appreciated, however, that it also finds utility in other therapy applications involving diagnostic imaging planning.

In radiation therapy, a radiation beam is focused on a tumor or other target from a plurality of directions. Ideally, the beam will irradiate the entire target with a selected radiation dose while avoiding or minimally irradiating surrounding critical tissues. In order to plan a radiation therapy session that is as close to ideal as possible, a 3D diagnostic image is generated and segmented. That is the contour and boundaries of the target, the critical surrounding tissue, bones or other dense radiation absorptive structures, are determined and delineated.

Manual contouring in radiation therapy (radiotherapy) planning is tedious and error prone. Automation of aspects of radiotherapy planning is desired as is illustrated by previous work in the field. Monte Carlo techniques are known in the art for dosimetry in intensity modulated radiation therapy. See, for example: Fix. M., "Monte Carlo Models for Dosimetry in Photon Beam Radiotherapy", Dissertation 2001, ETHZ, Zuerich. Sampling algorithms for segmentation are known in the computer vision community. See, for example, Isard, M. and Blake, A. "Condensation—Conditional Density Propagation for Visual Tracking", *International Journal of Computer Vision*, vol 28(1) pp 5-28. The use of sampling algorithms to analyze uncertainty in functional parameters (in the heart) has also been proposed. See, for example, international publication WO 2005/071615A1, to J. Sénégas, "Stochastic Analysis of Cardiac Function." Much effort is being put into the development of accurate automatic and/or semi-automatic segmentation algorithms. It is ambiguous, however, how much accuracy is needed in the contouring and how much influence slight variations in the delineation have on the plan. Resultantly, the uncertainty in the segmentation (delineation) must be propagated to evaluate measures derived from a given plan.

Even if a perfect delineation of the target organs is available, errors due to organ motion during treatment (such as breathing), set-up errors (e.g. patient positioning for treatment), computation of dosimetry (e.g. errors in Hounsfield values or in further patient or radiation treatment device dependent parameters that are required to compute the dose), and delivery inaccuracies need to be taken into account to evaluate the plan. In the following, the descriptions of the present application focus on delineation uncertainties, but the aforementioned uncertainties can be addressed as well in a similar manner.

Treatment plans in radiotherapy are evaluated by studying different measures derived from the dose distribution of the plan, e.g. cumulative dose volume histograms (DVHs), isodose curves, dose distribution statistics, and the like. These measures, however, ignore uncertainties and inaccuracies in contouring. Therefore, a measure, e.g. the minimum dose in the target planning volume, might change considerably with only a small change in the original contour on which the plan was based. This change may not be reflected in the measure reported to a radiation oncologist or other clinician or healthcare provider. Even with the ongoing improvement of the automatic segmentation algorithms, residual uncertainties due to the aforementioned effects may still affect the quality of the treatment plan. An evaluation of the treatment plan needs to reflect these uncertainties to eventually improve the treatment plan.

The present application provides a new and improved method and apparatus for radiation therapy planning, which overcomes the above-referenced problems and others.

In accordance with one aspect, a method of planning radiotherapy treatment is provided. An initial delineation of a target structure within a patient is generated. An optimal radiotherapy plan is created from the initial delineation of the target. A plurality of alternate delineations of the optimal radiotherapy plan are generated. A target measure such as a dose volume histogram is produced for each alternate segmentation (keeping the plan fixed). Statistics of the target measure, such as the mean and the standard deviation, are calculated from the target measures of the alternate delineations. The target measure statistics are displayed to a user.

In accordance with another aspect, a radiotherapy planning apparatus is provided. A planning image data memory stores diagnostic images of a subject for use in creating a radiotherapy plan for a subject. A model database contains previously constructed models of areas of interest, e.g. statistical shape models of organs. A radiotherapy planning processor constructs a radiotherapy plan based on the images of the subject and at least one model of the area of interest. Finally, a display displays at least one aspect of the radiotherapy plan to a user of the radiotherapy planning apparatus. An apparatus provides new optimization criteria to optimize the treatment plan. For example, a user could prepare two plans and prefer the one that performs the best on average, or has the least drastic worst outcome, or has the best 90% confidence interval.

In accordance with another aspect, a method of oncological treatment is provided. A target structure is initially segmented, defining a contour of the target structure. An initial treatment plan is computed from the initial segmentation of the target structure. A target measure is calculated for each portion of the segmented target structure. Statistics of the target measure are calculated for the entire target structure. A user is solicited for approval of the initial treatment plan. After the plan is approved, the target structure is treated with the approved plan.

One advantage lies in improved evaluation of radiotherapy plans.

Another advantage lies in quantified uncertainty in tissue contouring and radiotherapy.

Another advantage lies in propagating segmentation uncertainty in order to evaluate variability in radiation therapy planning.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
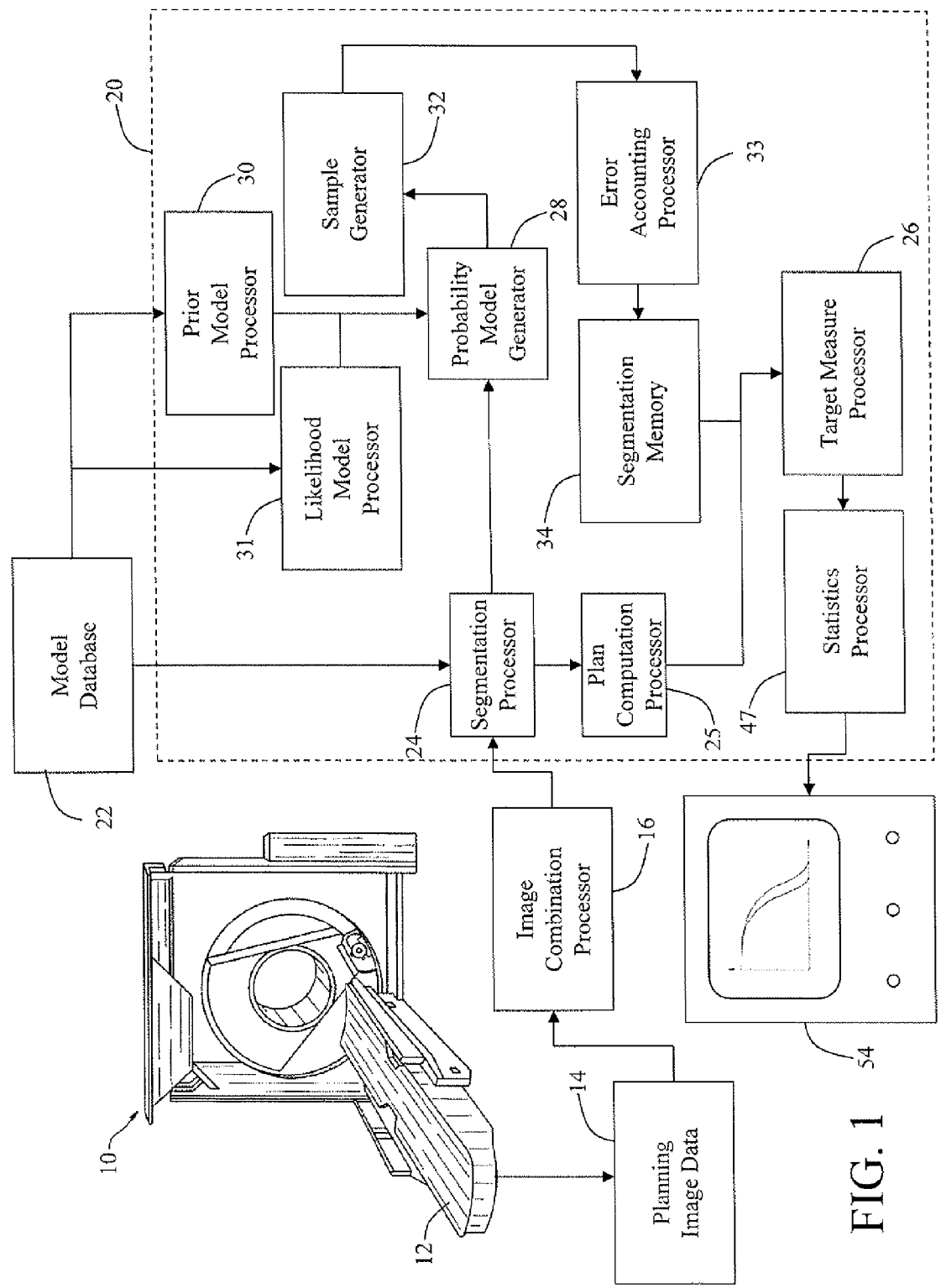
FIG. 1 is a diagrammatic illustration of a radiation therapy planning device in accordance with the present application.

By calculating probability distributions of dose distribution measures, a radiotherapy plan can account for the inherent uncertainty in organ contouring, in dose distribution due to organ motion, patient positioning, and delivery inaccuracies, and in dose distribution computation. This considerably improves plan evaluation and comparison. For example, a plan for which the minimum dose in the target volume is 50±10 gray (average±standard deviation) would be worse than a plan for which the minimum dose in the target volume is 48±2 gray. That is, the probability that the target will be hit with at least 45 gray is much higher with the latter plan. Furthermore, such analysis gives important information about the requirements (e.g. with respect to precision) to automatic segmentation algorithms.

When radiotherapy is prescribed for a patient, typically the patient receives a large dose of radiation that is administered regularly (e.g. daily) over an extended time span, on the order of several weeks. Treatment is so distributed for several reasons. One reason is to lessen system shock and collateral damage to healthy tissue by distributing the dose over a long period of time. Additionally, it gives the body an opportunity to metabolize dead target cells, better exposing remaining target cells to the radiation. During a treatment session, the patient is disposed in a targeting region of a radiation therapy device. This device is sometimes referred to as a linear accelerator or "linac." The position of the patient with respect to the radiation therapy device is only known up to a given accuracy. Moreover, motion of the patient and/or of the target organs after positioning is likely. As a consequence, the dose delivered to the target organ may differ from the optimal computed dose. For example, for a tumor that moves with breathing in the left-right direction, treating with an anterior-posterior beam could lead to worse target coverage than treatment with a lateral beam. This error source can be accounted for by modeling the breathing movement, e.g. on the basis of registered 4D CT images. The device typically administers a beam of x-rays, but other forms of high-energy, ionizing and penetrating radiation or accelerated particles may be appropriate, such as gamma rays, electrons, alpha particles, protons, and the like, depending on the diagnosis. A radiation emitter is mounted on a movable gantry to provide the emitter with a wide arc of approach angles to the patient. A subject support platform is preferably constructed of radio transparent material so the linac might also administer treatment from below the patient as well as above.

During radiotherapy treatment, several angles of approach to the target are used. This allows the total dose administered to a patient during a treatment session to be distributed over several approach paths that intersect at the target. This maximizes the administered radiation at the target while minimizing collateral damage to healthy tissue along the approach paths. Depending on the patient's particular needs, the radiation emitter can be collimated with a subject specific collimator that limits the radiation beam to a certain geometry, or splits the beam into several smaller "beamlets." A different collimator can be used for each angle of approach, as each view may have a slightly different profile view of the target, depending on the size and shape of the target and any adjacent radiation sensitive tissues. Residual errors in the angles used for radiation emission lead to inaccuracies in the dose distribution.

With reference to FIG. 1, before radiation treatment is ever administered to a patient, the patient first undergoes a planning process that designates the most beneficial treatment strategy for the patient's particular ailment. Radiotherapy planning is typically done in a separate locale than the actual radiotherapy device. This allows the radiotherapy device to operate uninterrupted, increasing patient throughput. Radiotherapy planning is typically done in a separate imaging suite that is remote from the actual location of the radiotherapy machine. Adaptive planning, however, is also utilized in fine tuning an already-developed radiotherapy plan. After a plan has been created for a patient, but before radiation treatment actually begins, the patient is physically brought to the treatment suite. This generally occurs right before their first scheduled treatment for convenience. One or more low power projection images of the region are taken with the patient situated in the linac. These images are used to verify the radiotherapy plan, and to make minor adjustments to the radiotherapy plan to account for minor differences in the positioning of the patient, minor changes in the patient's anatomy since the planning, and the like. Similarly, a radiotherapy plan can be adapted as treatment is ongoing. For example, an irradiated tumor often shrinks over the course of radiotherapy treatment. Projection images taken periodically throughout treatment can be used to verify the success of the treatment, and perhaps to alter the beam breadth or shape based on the new shape of the tumor.

Typically, one or more imaging modalities (e.g. CT, x-ray, MRI, PET) 10 are used to generate images of the patient on a support 12 that are used in the planning process. Frequently, more than one modality is used, and combination images are used to develop the radiotherapy plan. These modalities can be physically located in the planning suite, but also can be located in their own designated suites. For example, a CT scanner could be physically in the planning suite, but if a radiation oncologist desired additional images from different modalities to help plan, these images could be procured elsewhere. The planning images can be stored in a planning image memory 14 until needed. Optionally, images from different modalities can be merged by an image combination processor 16 to produce hybrid images. A PET/CT combination image is one example of a hybrid image, but is to be understood that a plurality of image combinations are possible. Often, the combination of images is realized by means of registration algorithms, which are prone to errors. The hybrid images are often beneficial to use in oncology planning because the benefits of multiple modalities can make the target more definite, contrasting it with surrounding tissue. The better a target is defined in pre-treatment planning, the more precisely its contour can be determined and the more precise the treatment plan can be with respect to dose, beam geometry, approach paths, etc.

The planning images are then analyzed by a radiotherapy planning processor 20. The end result provides a radiation oncologist with a treatment plan that the oncologist can approve, modify, or reject, as applicable. A more detailed discussion of the radiotherapy planning processor 20 follows below.

Once the oncologist determines the treatment plan, the plan can be verified using the previously generated and contoured images or through a set of supplemental images of the patient. The patient is positioned in the radiation treatment device or a simulator. Operating at a reduced power, a radiation beam is projected at each proposed angle. A detector is positioned on the other side of the patient to generate a shadowgram, that is, a mega electron volt (MeV) image or a projection image, along each proposed beam angle. This shadowgram is used to make fine adjustments to the beam angles and cross-sections. The angles and cross sections are marked for use in subsequent therapy sessions. Shadowgrams can also be used before or during each therapy session for verification and fine tuning.

The dose delivered to a segmented organ can be determined. But the accuracy of the dose delivered to the target is dependent on the accuracy with which the target contour was segmented. Further, the accuracy of the dose delivered is affected by organ motion during treatment, by the actual position of the patient during radiation, and by the delivery accuracy of the radiation system. It is also dependent on the accuracy of the other input parameters used by the dose computation system, such as Hounsfield values. It is desirable to yield probability densities for measures derived from dose distributions. The probability densities reflect the variability that is due to uncertainty in organ contouring and the other aforementioned uncertainties. Statistics of dose distribution measurements can be computed from the probability densities. The computable statistics include average and standard deviation, quantiles (1%, 5%, median, 95%, 99%) of dose, confidence intervals of dose, and the like. These densities can be visualized as figures or numbers. They can also be visualized as color maps overlaid on the diagnostic images. In order to compute probability densities of the treatment plan, a segmentation processor 24 first segments the planning images. The segmentation is preferably performed within a Bayesian segmentation framework in which the uncertainty of the delineated contours is described by means of a prior model of the contour (e.g. organ model) and a likelihood model of the planning image itself (observation model). Possible segmentation frameworks are described in U.S. Pat. No. 6,735,277 to McNutt, et al., and in co-pending provisional application 60/807,531 to Kaus, et al. These organ models and likelihood models can be stored in a model database 22 and retrieved when needed by a segmentation processor 24.

After the planning images are segmented, a treatment plan is computed by a plan computation processor 25, and a target measure, e.g. a dose volume histogram, is created by a target measure processor 26. Current approaches for automatic segmentation make use of probability models, usually within a Bayesian segmentation framework. Generally, as the accuracy of the segmentations increases, resulting target measures of the dose will also improve in confidence. In this framework, a probability model of the segmented organ given the planning images used for segmentation is desired. Thus, using a Bayesian framework, the prior and the likelihood models, a probability model generator 28 generates a probability model. This probability model is also referred to as the posterior probability. Knowledge about the organ/tumor/target volume is embedded into a prior model of the segmented shape, which e.g., can be derived by a prior model processor 30 on the basis of the model database 24. Furthermore, a likelihood model of the observation (image) given the segmented shape is formulated by a likelihood model processor 31. If images from several modalities are used for planning, the likelihood model takes into account all the available images, and possibly accounts for errors due to the combination of images, such as registration errors. The prior model and the likelihood model are combined to form the posterior probability model.

Next, a sample generator 32 generates samples from the probability model that was previously generated. This ensures that the inherent uncertainty about the segmentation is directly taken into account. Each sample generated by the sample generator 32 can be understood as a likely segmentation. That is, there is a non-negligible probability that the segmentation will represent the actual conditions. Different methods, such as importance sampling or Markov Chains, can be used to generate a sample that follows the probability model. See Doucet, et al., "Sequential Monte Carlo in Practice" Springer, 2001; and Gilks et al., "Markov Chains Monte Carlo in Practice, Chapman and Hall, 1996. For example, in importance sampling, the samples are directly sampled from the prior model and are weighted according to the likelihood model. Furthermore, the generated sample is possibly modified to take into account further errors, such as radiation scatter, motion, set-up errors, dosimetry, and delivery inaccuracies. This is performed by an error accounting processor 33. For example, errors due to patient positioning and/or displacement and organ motion can be taken into account by adding to each sample a random perturbation, such as a random translation, rotation, and the like. This random perturbation can be described by a probability model that is part of the error accounting processor. Each generated segmentation is stored in a segmentation memory 34. For each generated sample, the target measure (e.g. quantiles of a dose volume histogram (DVH)) is computed by the target measure processor 26. This yields a sample of the target measure. Uncertainties in the dose delivery or in the dose computation can be accounted for at this stage. This can be done by using a probability model describing the precision of each of the involved parameters, such as Hounsfield values or angles of approach for the radiation emission. Values following the probability model of the parameter are generated, and for each of these values, the corresponding dose distribution for the current sample is computed. From the dose distribution, a sample of the target measure is derived. Finally, all the samples of the target measure are fed back to a statistics processor 47 and a histogram (or any other statistical descriptor) is computed thereby. This is known as Monte Carlo integration. This histogram or other descriptor reflects the variability in the target measure due to the uncertainty in the segmentation. This descriptor can be displayed to the user on a display device 54.

Figure 2:
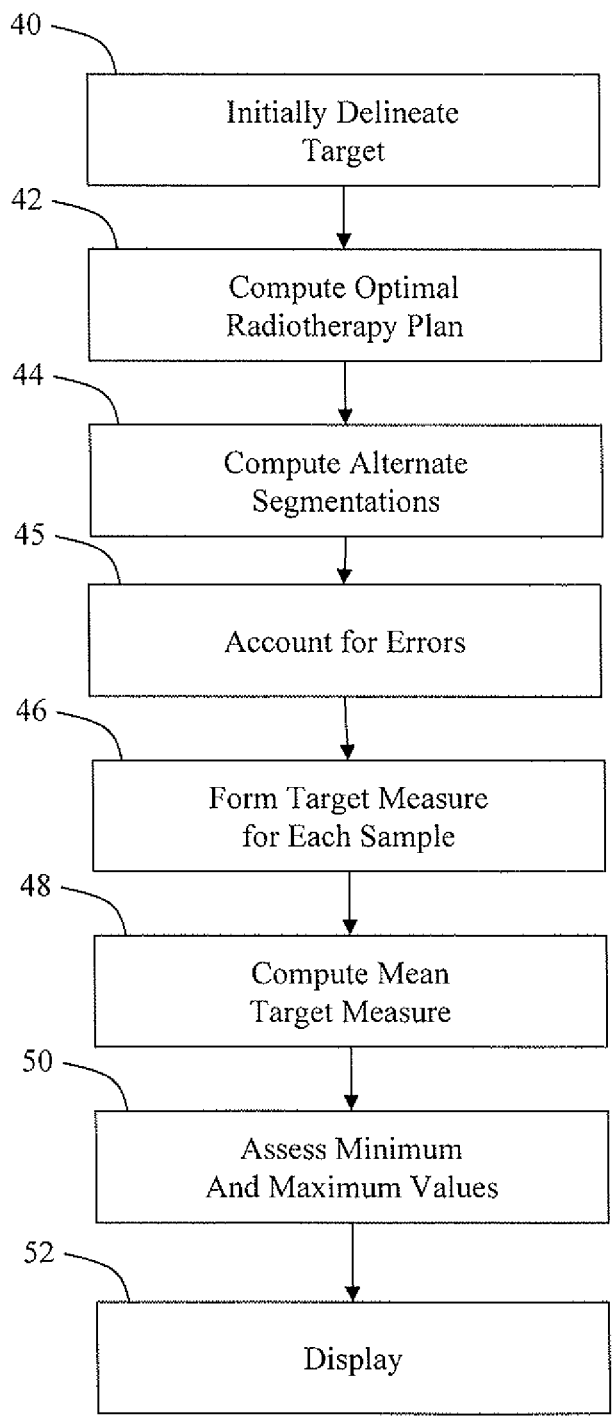
FIG. 2 is a flow diagram of steps in creation of a radiotherapy plan in accordance with the present application.

With reference now to FIG. 2, the radiotherapy plan will be described by reference to a flow diagram. An initial delineation of the target 40 (that is, a tumor, an at-risk organ, or the like) is obtained. Preferably, this is done automatically, such as by using an algorithm that performs the segmentation steps outlined above, but in the alternative, it can be done manually by a clinician outlining the region by hand with a pointing device. From this initial contouring, an optimal radiotherapy plan is computed 42 using the appropriate planning software. Then, using the probability model described above, an ensemble of alternative segmentations is generated 44. Each sample is associated with a probability. The sampling can be performed from the initial automatic delineation of contours. Further errors, such as radiation scatter, motion, set-up errors, dosimetry, and delivery inaccuracies, are accounted for 45. This is performed by the error accounting processor 33, which modifies the sample accordingly. For each sample, any suitable target measure, such as a DVH, is computed 46 on the basis of the initial radiotherapy plan. From the ensemble of samples of the target measure, suitable statistics characterizing this measure are computed by the statistics processor 47, such as a mean target measure 48, as well as confidence intervals of the target measure. The probability that the minimum dose in the target organ is under a given level can also be assessed, or the probability that the maximum dose in a risk organ is above a given threshold 50. This additional information is eventually presented to the clinician in a graphical manner 52 on a display 54.

Figure 3:
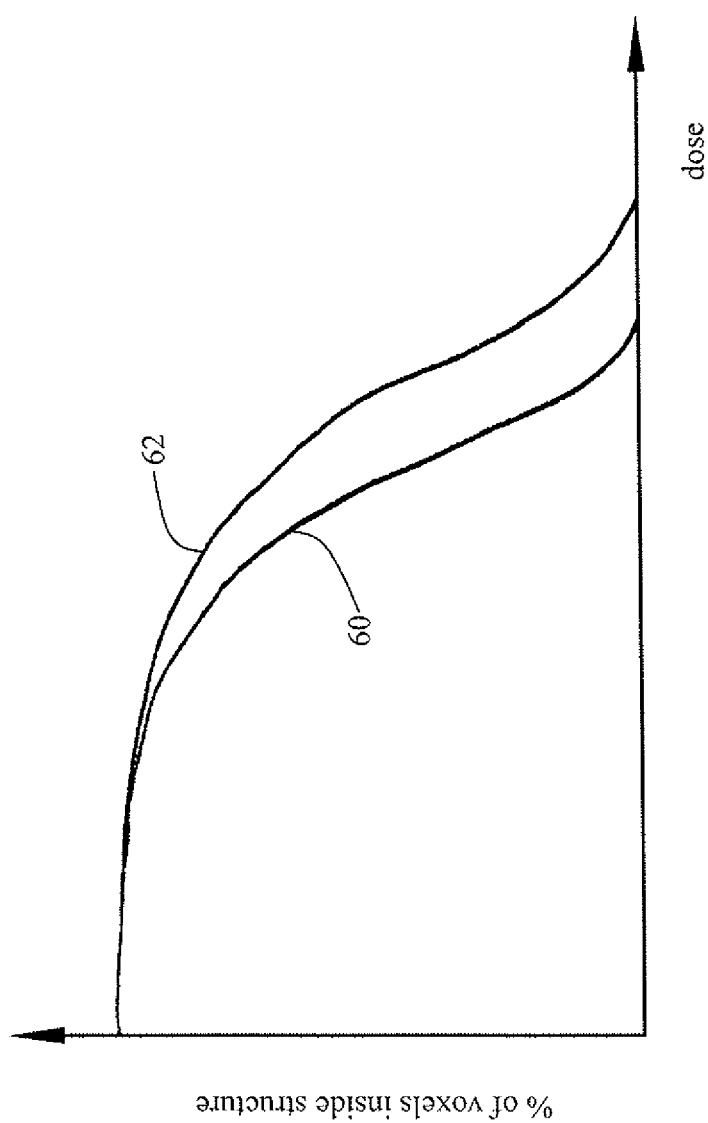
FIG. 3 is an exemplary histogram range display.

An exemplary display of this information is represented in FIG. 3. Two curves are presented to the clinician. A first curve 60 represents a dose minimum, that is, the minimum amount of radiation that the target region will receive according to the present radiotherapy plan. A second curve 62 represents the maximum amount of radiation that the target region will receive. The curves take into account the possible inaccuracies due to organ contouring in the diagnostic images and the further inaccuracies analyzed by the error accounting processor 33. The output to the user can be in the form of the curves of FIG. 3, or an image of the dose distribution statistics overlaid on a diagnostic image of the organs, or the like. It is desirable that the cumulative dose volume histogram of the target structure will be between the minimum and maximum curves 60, 62. The clinician can decide one the basis of these statistics whether the plan is acceptable. Furthermore, different plans can be compared on the basis of statistical hypothesis tests. For example, the clinician can investigate statistical differences that result from slightly varying certain aspects of the plan. The clinician can adjust the selected trajectory, angles of approach, method of organ contouring, and the like. By varying these components, the statistical dose probabilities will also vary slightly. By investigating fine tuning in the plan, statistical hypotheses could aid the clinician in choosing between alternative plans. For example, the clinician could statistically assess whether one plan is significantly better (safer, more efficient, more effective, and the like) than another plan.

In the alternative, a treatment plan could be adapted according to the generated contours. After a treatment plan is computed from the initial segmentation, and the viability of the plan is assessed, a feedback loop could be incorporated to compute/choose a treatment plan that has a lower variability. Also, the generated samples could be used for the treatment plan optimization, in a manner similar to simulated annealing.

Even though the entire process of developing a radiotherapy plan is preferably automated, approval of the plan lies with the radiation oncologist or other health care professional. The oncologist is able to accept the plan, modify the plan, or reject the plan. Given that the calculations are heavily dependant on the underlying diagnostic images, the oncologist may desire to take new images of the patient in an attempt to generate a more satisfactory radiotherapy plan.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method of planning radiotherapy treatment comprising:
   generating an initial delineation of a target structure within a patient with a segmentation processor;
   creating an optimal radiotherapy plan from the initial delineation of the target structure with a radiotherapy planning processor;
   creating a plurality of alternate delineations of the target structure with the segmentation processor;
   producing a target measure for each alternate delineation by a target measure processor;
   calculating at least one statistic from the target measures of the alternate delineations with a statistic processor;
   displaying the statistic to a user on a display.

2. The method as set forth in claim 1, further including:
   assessing a viability of a treatment plan by calculating a probability that a dose exceeds a given threshold.

3. The method as set forth in claim 2, further including:
   adapting the treatment plan to create a more viable treatment plan based upon the at least one statistic.

4. The method as set forth in claim 1, further including:
   accounting for errors in the calculation of at least one of dose delivery, organ motion, set up parameters, patient positioning, and radiation scatter.

5. The method as set forth in claim 1, wherein the step of creating a plurality of alternate delineation includes:
   associating each delineation with a probability.

6. The method as set forth in claim 1, wherein the step of generating an initial delineation includes:
   a user manually defining the initial delineation.

7. The method as set forth in claim 1, wherein the step of generating an initial delineation includes:
   generating the initial delineation with an automatic or semi-automatic segmentation algorithm.

8. The method as set forth in claim 7, wherein the automatic segmentation algorithm utilizes knowledge of a target structure based on prior models of the target structure and a likelihood model of the image data given the target structure.

9. The method as set forth in claim 1, wherein the step of calculating at least one statistic of the target measure includes:
   averaging the values of the target measures of the alternate delineations to obtain a mean target measure;
   computing a standard deviation, quantiles, and confidence intervals of the target measure; and
   performing a statistical test on the computed target measure.

10. The method as set forth in claim 9, wherein the step of displaying includes at least one of displaying a figure, displaying numerical values, displaying an overlay of average dose isocontours, displaying a minimum dose isocontour, and displaying a maximum dose isocontour for the at least one statistic.

11. A radiotherapy planning apparatus comprising:
   a planning image data memory for storing diagnostic images of a subject for use in creating a radiotherapy plan for the subject;
   a model database that contains previously constructed models of areas of interest;
   a segmentation processor which generates an initial segmentation and alternative segmentations of the areas of interest;
   a radiotherapy planning processor that constructs an initial radiotherapy plan based on an initial segmentation of images of the subject and at least one model of the area of interest;
   a target measure processor which produces a target measure for each alternative segmentation;
   a statistic processor which calculates at least one statistic from the target measures of the alternative segmentations; and
   a display for displaying at least one aspect of the radiotherapy plan and the at least one statistic to a user.

* * * * *